(12) United States Patent
Takagi

(10) Patent No.: US 11,564,871 B2
(45) Date of Patent: Jan. 31, 2023

(54) DISPERSION OF FINE LIPID PARTICLE DISPERSION

(71) Applicant: KAO CORPORATION, Tokyo (JP)

(72) Inventor: Shunsuke Takagi, Shinagawa-ku (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 16/958,541

(22) PCT Filed: Dec. 28, 2018

(86) PCT No.: PCT/JP2018/048404
§ 371 (c)(1),
(2) Date: Jun. 26, 2020

(87) PCT Pub. No.: WO2019/131987
PCT Pub. Date: Jul. 4, 2019

(65) Prior Publication Data
US 2021/0059910 A1    Mar. 4, 2021

(30) Foreign Application Priority Data

Dec. 28, 2017 (JP) .............................. JP2017-254874

(51) Int. Cl.
A61K 8/04 (2006.01)
A61K 8/34 (2006.01)
A61K 8/42 (2006.01)
A61K 8/46 (2006.01)
A61K 8/63 (2006.01)
A61K 8/92 (2006.01)
A61Q 19/00 (2006.01)

(52) U.S. Cl.
CPC ................ A61K 8/04 (2013.01); A61K 8/345 (2013.01); A61K 8/42 (2013.01); A61K 8/466 (2013.01); A61K 8/63 (2013.01); A61K 8/922 (2013.01); A61Q 19/00 (2013.01); A61K 2800/413 (2013.01)

(58) Field of Classification Search
None
See application file for complete search history.

(56) References Cited

U.S. PATENT DOCUMENTS

| 2002/0010215 | A1 | 1/2002 | Shiroyama et al. |
| 2006/0057091 | A1 | 3/2006 | Fujii et al. |
| 2006/0210522 | A1 | 9/2006 | Ishida et al. |
| 2011/0182999 | A1 | 7/2011 | Serizawa et al. |
| 2020/0078272 | A1 | 3/2020 | Naito et al. |

FOREIGN PATENT DOCUMENTS

| EP | 1 153 595 A2 | 11/2001 |
| JP | 2-191208 A | 7/1990 |
| JP | 9-124432 A | 5/1997 |
| JP | 2001-316217 A | 11/2001 |
| JP | 2002-87931 A | 3/2002 |
| JP | 2004-331595 A | 11/2004 |
| JP | 2006-281038 A | 10/2006 |
| JP | 2006-335693 A | 12/2006 |
| JP | 2007-15972 A | 1/2007 |
| JP | 2013-227294 A | 11/2013 |
| JP | 2015-93840 A | 5/2015 |
| WO | WO 2004/045566 A1 | 6/2004 |
| WO | WO 2004/098557 A1 | 11/2004 |
| WO | WO 2010/038814 A1 | 4/2010 |
| WO | WO 2015/152420 A1 | 10/2015 |
| WO | WO 2018/123883 A1 | 7/2018 |

OTHER PUBLICATIONS

International Search Report dated Mar. 19, 2019 in PCT/JP2018/048404 filed Dec. 28, 2018, 2 pages.
Extended European Search Report dated Sep. 24, 2021 in European Patent Application No. 16893406.1, 8 pages.

Primary Examiner — Kyung S Chang
(74) Attorney, Agent, or Firm — Oblon, McClelland, Maier & Neustadt, L.L.P.

(57) ABSTRACT

To provide a composition in which fine particles of solid lipid such as ceramides are emulsified and dispersed in a stable manner without being crystalized. A dispersion of fine lipid particles containing the following components (A) to (E), wherein the dispersion has a pH of 3.5 or more and 8.0 or less and the fine lipid particles have a heat of fusion of 0.30 J/g or less in a temperature range of 45° C. or more and 80° C. or less and an average particle size of less than 200 nm. (A) one or more selected from the group consisting of a sterol and a derivative thereof, (B) a lipid other than the component (A), the lipid being solid or semi-solid at 25° C., (C) an anionic surfactant, (D) a water-soluble solvent and (E) water.

7 Claims, No Drawings

DISPERSION OF FINE LIPID PARTICLE DISPERSION

FIELD OF THE INVENTION

The present invention relates to a dispersion of fine lipid particles and a skin cosmetic.

BACKGROUND OF THE INVENTION

A lipid called stratum corneum intercellular lipid exists in the gap defined between corneocytes constituting the stratum corneum, which exists in the outermost layer of the skin. Ceramide accounts for about 50% of the composition of the stratum corneum intercellular lipid, the rest including cholesterol, cholesterol ester and fatty acid. Of them, ceramide is deeply associated with, for example, rough skin and dry skin, and it is known that the condition of the stratum corneum can be improved by supplementing ceramide externally.

Various cosmetics prepared by compounding solid lipid such as ceramides were reported in this view. These solid lipids, however, are highly crystalline and have high melting point, and thus stabilizing them in a formulation is difficult. Thus, various methods for stabilization were developed. Reports include, for example, a ceramide dispersion prepared by combining ceramide-containing particles, fatty acid having a melting point of 30° C. or less, a nonionic surfactant, an anionic surfactant and other components (Patent Literature 1); a single phase microemulsion composition containing a nonionic surfactant, oil, polyoxypropylene-polyoxyethylene copolymer dialkyl ether and water (Patent Literature 2); a lipid composition prepared by mixing ceramides and aliphatic alcohol having 12 to 30 carbon atoms and compatibilizing them at 90° C. (Patent Literature 3); a thermosensitive cholesteric liquid crystal composition containing five components including cholesterol fatty acid ester (Patent Literature 4); and a technique for preparing a liquid crystal emulsion by heating ceramide, cholesterol and other components at a phase transition temperature or more, adding polyhydric alcohol thereto, and then cooling the mixture (Patent Literature 5).

(Patent Literature 1) International Publication No. 2010/38814
(Patent Literature 2) JP-A-2007-15972
(Patent Literature 3) JP-A-2004-331595
(Patent Literature 4) JP-A-hei 2-191208
(Patent Literature 5) JP-A-hei 9-124432

SUMMARY OF THE INVENTION

The present invention provides:
a dispersion of fine lipid particles, comprising the following components (A) to (E), wherein the dispersion has a pH of 3.5 or more and 8.0 or less and the fine lipid particles have a heat of fusion of 0.30 J/g or less in a temperature range of 45° C. or more and 80° C. or less and an average particle size of less than 200 nm:
(A) one or more selected from the group consisting of a sterol and a derivative thereof,
(B) a lipid other than the component (A), the lipid being solid or semi-solid at 25° C.,
(C) an anionic surfactant,
(D) a water-soluble solvent, and
(E) water.

DETAILED DESCRIPTION OF THE INVENTION

The problem with solid lipids such as ceramides in the compositions as described above is that they are crystallized, resulting in relatively large and unstable crystals, and that when solid lipids are in the state of liquid crystal, they are often unstable in the formulation. Therefore, cosmetics using the above compositions could not fully exhibit the effect of solid lipids such as ceramides over time.

Meanwhile, the surface of the skin is kept weekly acidic in order to maintain homeostasis. Thus, to design a low irritant skin cosmetic, it is ideal that the formulation be prepared to be weekly acidic or have a pH close to that of the skin. However, the problem is that, when a specific anionic surfactant is used to emulsify and disperse solid lipid such as ceramides in a stable manner, the surfactant has a particularly high surface activity in an alkali environment, while the surface activity is lost at a weakly acidic to neutral range of pH.

Thus, an object of the present invention is to provide a dispersion of fine lipid particles in which fine particles of solid lipid such as ceramides are emulsified and dispersed in a stable manner without being crystallized even in an acidic condition.

In view of the above, the present inventors conducted various studies on finely dispersing solid lipid such as ceramides and means for preventing crystallization of the solid lipid, and as a result, found that a dispersion of fine lipid particles in which fine particles of solid lipids such as ceramides are emulsified and dispersed in a stable manner with low crystallinity can be obtained by using sterols and a solid lipid such as ceramides in combination and incorporating an anionic surfactant and a water-soluble solvent into the dispersion when a specific anionic surfactant is used, even in an acidic condition as well as a neutral to alkaline condition.

In the dispersion of fine lipid particles of the present invention, fine particles of solid lipid such as ceramides are emulsified and dispersed in a stable manner with low crystallinity even in an acidic condition. Since fine particles of solid lipid such as ceramides are emulsified and dispersed in a stable manner with low crystallinity, the solid lipid exhibits a sufficient effect on the skin.

The component (A) used for the dispersion of fine lipid particles of the present invention is one or more selected from a sterol and a derivative thereof. The component (A) contributes to reducing the crystallinity of lipid of the component (B) and reducing the particle size thereof to stabilize the particles in the dispersion of fine lipid particles of the present invention.

Examples of the components (A) include a cholesterol, a phytosterol and a derivative thereof. Examples of derivatives of the cholesterol and the phytosterol include fatty acid cholesterol esters and fatty acid phytosterol esters. Here, a cholesterol ester of fatty acid having 12 to 24 carbon atoms is preferred as the fatty acid cholesterol ester. More specifically, one or more selected from the group consisting of cholesteryl laurate, cholesteryl palmitate, cholesteryl myristate, cholesteryl oleate, cholesteryl isostearate and cholesteryl linoleate are preferred. Furthermore, sterol esters of N-acylamino acid may be used, such as di(cholesteryl/behenyl/octyldodecyl) N-lauroyl-L-glutamate, di(cholesteryl/octyldodecyl) N-lauroyl-L-glutamate, di(phytosteryl/behenyl/octyldodecyl) N-lauroyl-L-glutamate, di(phytosteryl/octyldodecyl) N-lauroyl-L-glutamate, di(phytosteryl/octyldodecyl) N-lauroyl-L-glutamate, and (phytosteryl/decyltetradecyl) N-myristoyl-N-methylalanine. Preferred examples thereof include di(cholesteryl/octyldodecyl) N-lauroyl-L-glutamate and di(phytosteryl/octyldodecyl) N-lauroyl-L-glutamate. Examples of commercially available products of the sterol esters of N-acylamino acid include "ELDEW PS-203," "Plandool-LG2" (di(phytosteryl/octyldecyl) N-lauroyl-L-glutamate), "ELDEW CL-301" (di(cholesteryl/behenyl/octyldodecyl) N-lauroyl glutamate), "ELDEW CL-202" (di(cholesteryl/octyldodecyl) N-lauroyl glutamate), "ELDEW PS-304", "ELDEW PS-306", "Plandool-LG1", "Plandool-LG3", "Plandool-LG4" (di(phytosteryl/behenyl/octyldodecyl) N-lauroyl glutamate), and "ELDEW APS-307" ((phytosteryl/decyltetradecyl) N-myristoyl-N-methylalanine), available from Ajinomoto Co., Inc. and NIPPON FINE CHEMICAL CO., LTD.

One or more of these may be used as the component (A). To reduce the crystallinity and the particle size of the component (B) so as to stabilize the particles, the dispersion of fine lipid particles of the present invention contains preferably 0.003% by mass or more, more preferably 0.08% by mass or more, further preferably 0.2% by mass or more, even more preferably 0.3% by mass or more, and still more preferably 0.4% by mass or more of the component (A). From the same point of view, the dispersion contains preferably 5.0% by mass or less, more preferably 1.0% by mass or less, further preferably 0.8° by mass or less, and even more preferably 0.6% by mass or less of the component (A). More specifically, the dispersion contains preferably 0.003% by mass or more and 5.0% by mass or less, more preferably 0.08% by mass or more and 1.0% by mass or less, further preferably 0.2% by mass or more and 0.8% by mass or less, even more preferably 0.3% by mass or more and 0.8% by mass or less, and still more preferably 0.4% by mass or more and 0.6% by mass or less of the component (A).

The component (B) is a lipid other than the component (A), and is solid or semi-solid at 25° C. As used herein, being solid or semi-solid at 25° C. means that the lipid has a viscosity at 25° C. of more than 10,000 mPa·s. The viscosity is measured by a B-type viscometer (VISCOMETER TVB-10 manufactured by Toki Sangyo Co., Ltd.) with rotor No. 4 at 12 rpm for 1 minute. The component (B) is an active ingredient of the cosmetic and has the effect of, for example, moisturizing the skin and improving the barrier function of the skin. Examples of solid or semi-solid lipids include lipids having a melting point of from 50 to 150° C. Examples of the component (B) include ceramides, sphingolipids such as sphingosines (including natural and synthetic ones), fatty acids having 16 to 22 carbon atoms such as stearic acid and behenic acid, and aliphatic alcohols having 12 to 30 carbon atoms such as cetyl alcohol, stearyl alcohol, behenyl alcohol, batyl alcohol and chimyl alcohol.

Examples of ceramides include natural ceramides, sphingosine derivatives, and structurally analogous substances (synthetic ceramides) disclosed in JP-A-sho 62-228048, JP-A-sho 63-216812, JP-A-sho 63-227513, JP-A-sho 64-29347, JP-A-sho 64-31752 and JP-A-hei 8-319263. More specifically, compounds selected from the following formulas (1) and (2) are preferred, and compounds of the following formula (1) are particularly preferred.

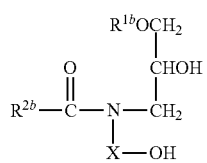

(1)

wherein $R^{1b}$ represents a hydrocarbon group having 10 to 26 carbon atoms, $R^{2b}$ represents a hydrocarbon group having 9 to 25 carbon atoms, and X represents —$(CH_2)_n$— wherein n is an integer of from 2 to 6.

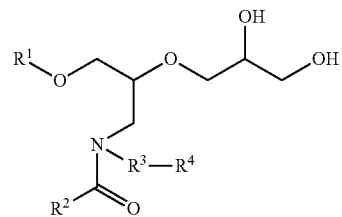

(2)

wherein $R^1$ and $R^2$ are the same or different and represent an optionally hydroxylated hydrocarbon group having 1 to 40 carbon atoms, $R^3$ represents an alkylene group having 1 to 6 carbon atoms or a single bond, $R^4$ represents a hydrogen atom, an alkoxy group having 1 to 12 carbon atoms or a 2,3-dihydroxypropyloxy group, with a proviso that, when $R^3$ is a single bond, $R^4$ is a hydrogen atom.

In the above formulas (1) and (2), an alkyl group or an alkenyl group is preferred as the hydrocarbon group.

Examples of compounds of the formula (1) include N-(hexadecyloxyhydroxypropyl)-N-hydroxyethylhexadecanamide. Examples of compounds of the formula (2) include a long chain dibasic acid bis-3-methoxypropylamide.

Of these compounds as the component (B), natural ceramides, synthetic ceramides of the formulas (1) and (2), and aliphatic alcohols having 12 to 30 carbon atoms are preferred in view of the moisturizing effect and the effect of improving barrier function. These lipids may be used singly or in combinations of two or more of them.

The dispersion of fine lipid particles of the present invention contains preferably 0.01% by mass or more, more preferably 0.1% by mass or more, and further preferably 0.3% by mass or more of the compound (B) in view of the moisturizing effect and the effect of improving barrier function. The dispersion contains preferably 5.0° by mass or less, more preferably 3.0° by mass or less, and further preferably 1.0% by mass or less of the component (B) in view of reduction of crystallinity and reduction of the particle size so as to stabilize the particles. The content is in a specific range of preferably 0.01% by mass or more and 5.0% by mass or less, more preferably 0.1% by mass or more and 3.0% by mass or less, and further preferably 0.3% by mass or more and 1.0% by mass or less.

The mass ratio of the component (A) to the component (B), (A/B), in the dispersion of fine lipid particles of the present invention is preferably 0.1 or more, more preferably 0.2 or more, and further preferably 0.3 or more, and preferably 1.0 or less, more preferably 0.8 or less, and further preferably 0.6 or less, in view of reduction of the crystallinity of the component (B) so as to stabilize the particles. The mass ratio is in a specific range of preferably 0.1 or more and 1.0 or less, more preferably 0.2 or more and 0.8 or less, and further preferably 0.3 or more and 0.6 or less.

The component (C) is an anionic surfactant. To have a sufficient surface activity at pH 3.5 to 8.0 covering not only alkaline or neutral conditions but also acidic conditions, an N-acylamino acid salt, an N-acylmethyltaurine salt, an alkyl phosphate, a polyoxyethylene alkyl ether phosphate, a fatty acid salt, an alkyl sulfate ester salt, a polyoxyethylene alkyl ether sulfate ester salt, an alkyl ether carboxylate, a dialkyl sulfosuccinate and a diacylamino acid lysine salt are preferred as an anionic surfactant. Of them, one or more selected from the group consisting of an N-acylamino acid salt, an N-acylmethyltaurine salt, a polyoxyethylene alkyl ether phosphate, a fatty acid salt, a diacylamino acid lysine salt, an alkyl sulfate ester salt, a polyoxyethylene alkyl ether sulfate ester salt, an alkyl ether carboxylate and a dialkyl sulfosuccinate are preferred. One or more selected from the group consisting of an N-acylamino acid salt, an N-acylmethyltaurine salt, a polyoxyethylene alkyl ether phosphate, a fatty acid salt, a diacylamino acid lysine salt, a polyoxyethylene alkyl ether sulfate, an alkyl ether carboxylate and a dialkyl sulfosuccinate are more preferred. One or more selected from the group consisting of an N-acylamino acid salt, an N-acylmethyltaurine salt, a polyoxyethylene alkyl ether phosphate, a fatty acid salt and a diacylamino acid lysine salt are further preferred, and one or more selected from the group consisting of an N-acylamino acid salt and an N-acylmethyltaurine salt are even more preferred.

Examples of the N-acylamino acid salts include an N-acyl glutamate and an N-acyl sarcosinate, such as sodium N-lauroyl-L-glutamate, sodium N-stearoyl-L-glutamate, arginine N-stearoyl-L-glutamate, sodium N-myristoyl-L-glutamate and sodium N-lauroyl sarcosinate. Examples of the N-acylmethyltaurine salts include sodium N-myristoyl-N-methyltaurate, sodium N-lauroyl-N-methyltaurate and sodium N-stearoyl-N-methyltaurate. Examples of the alkyl phosphates include sodium monomyristyl phosphate, sodium monostearyl phosphate and sodium di(C12-C15) pareth-8-phosphate. Examples of the polyoxyethylene alkyl ether phosphates include a sodium polyoxyethylene oleyl ether phosphate, sodium polyoxyethylene cetyl ether phosphate and sodium polyoxyethylene stearyl ether phosphate. Examples of the fatty acid salts include fatty acid salts having 12 to 24 carbon atoms such as sodium laurate, potassium palmitate and arginine stearate. Examples of the alkyl sulfate ester salts include sodium lauryl sulfate and potassium lauryl sulfate. Examples of the polyoxyethylene alkyl ether sulfates include polyoxyethylene lauryl sulfate triethanolamine. Examples of the alkyl ether carboxylates include polyoxyethylene lauryl ether acetate. Examples of the dialkyl sulfosuccinates include sodium di-2-ethylhexyl sulfosuccinate. Examples of the diacylamino acid lysine salts include sodium dilauroyl glutamate lysine. One or more of these anionic surfactants may be used.

The content of the component (C) in the dispersion of fine lipid particles of the present invention is preferably 0.002% by mass or more, more preferably 0.05% by mass or more, and further preferably 0.1° by mass or more, and preferably 3.0% by mass or less, more preferably 1.0% by mass or less, and further preferably 0.5% by mass or less in view of the stability of the formulation and homeostasis on the surface of the skin on which the dispersion is used. More specifically, the content is preferably 0.002% by mass or more and 3.0% by mass or less, more preferably 0.05% by mass or more and 1.0% by mass or less, and further preferably 0.1% by mass or more and 0.5% by mass or less.

The total mass of the component (A), the component (B) and the component (C) in the dispersion of fine lipid particles of the present invention is preferably 0.015% by mass or more, more preferably 0.33° by mass or more, and further preferably 0.5° by mass or more, and preferably 13.0% by mass or less, more preferably 5.0% by mass or less, and further preferably 2.0% by mass or less based on the total amount of the dispersion of fine lipid particles, in view of the moisturizing effect and the effect of improving barrier function. The total mass is in a specific range of preferably 0.015% by mass or more and 13.0% by mass or less, more preferably 0.33% by mass or more and 5.0% by mass or less, and further preferably 0.5% by mass or more and 2.0% by mass or less.

The ratio of the total mass of the component (A) and the component (B) to the mass of the component (C), ((A+B)/C), in the dispersion of fine lipid particles of the present invention is preferably 0.05 or more, more preferably 0.5 or more, and further preferably 1.0 or more, and even more preferably 2.0 or more, and preferably 6.0 or less, more preferably 5.5 or less, and further preferably 5.0 or less in view of the moisturizing effect, the effect of improving barrier function and stability. The ratio is in a specific range of preferably 0.05 or more and 6.0 or less, more preferably 0.5 or more and 5.5 or less, further preferably 1.0 or more and 5.5 or less, and even more preferably 2.0 or more and 5.5 or less.

The component (D) is a water-soluble solvent. The water-soluble solvent contributes to efficiently and homogeneously dissolving the component (A) and the component (B), or the component (A), the component (B) and the component (C) in the dispersion of fine lipid particles of the present invention, and to improving stability and controlling feeling on use. Examples of the water-soluble solvent (D) include polyhydric alcohols such as ethylene glycol, diethylene glycol, triethylene glycol, polyethylene glycol (average molecular weight: less than 1,000), propylene glycol, dipropylene glycol, polypropylene glycol (average molecular weight: less than 1,000), glycerol, diglycerol, polyglycerol, isoprene glycol, 1,2-pentanediol, 1,3-propanediol, 1,3-butylene glycol, hexylene glycol and methyl gluceth, and lower alcohols such as methanol and ethanol. Of them, glycerol, 1,3-butylene glycol, dipropylene glycol, 1,3-propanediol and the like are particularly preferred. One or more of these may be used as the component (D).

The content of the component (D) is preferably 1.0% by mass or more, more preferably 2.0% by mass or more, and further preferably 3.0% by mass or more, and preferably 30% by mass or less, more preferably 25% by mass or less, and further preferably 20% by mass or less, in the dispersion of fine lipid particles of the present invention, in order to dissolve the component (A) and the component (B), or the component (A), the component (B) and the component (C) efficiently and homogeneously, to improve stability and to control feeling on use. The content is in a specific range of preferably 1.0° by mass or more and 30% by mass or less, more preferably 2.0% by mass or more and 25% by mass or less, and further preferably 3.0% by mass or more and 20% by mass or less.

The dispersion of fine lipid particles of the present invention further comprises component (E), water. The content of (E) water in the dispersion of fine lipid particles of the present invention is preferably 50% by mass or more, more preferably 70% by mass or more, and further preferably 80% by mass or more, and preferably 97% by mass or less, more preferably 95% by mass or less, and further preferably 90% by mass or less in view of stability and feeling on use. The content is in a specific range of preferably 50% by mass or more and 97% by mass or less, more preferably 70% by mass or more and 95% by mass or less, and further preferably 80% by mass or more and 90% by mass or less.

It is preferable that the dispersion of fine lipid particles of the present invention further comprise a component (F), a nonionic surfactant, in consideration of stability. A nonionic surfactant having an HLB of from 10 to 20 is preferred, a nonionic surfactant having an HLB of from 12 to 15 is more preferred, and a nonionic surfactant having an HLB of from 12.5 to 14.5 is further preferred as the nonionic surfactant (F).

In this regard, the HLB (hydrophilic-lipophilic balance) can be calculated by, for example, the following equation.

Equation: [HLB]=7+1.171 log(Mw/Mo)

wherein Mw represents the molecular weight of the hydrophilic group of a surfactant, Mo represents the molecular weight of the hydrophobic group of the surfactant, and log represents a logarithm to base 10.

When two of a surfactant X and a surfactant Y are used in combination as nonionic surfactants, the HLB of the mixture of the two nonionic surfactants may be calculated by the equation:

Equation: [HLB]=[($W_X$×$HLB_X$)+($W_Y$×$HLB_Y$)]/($W_X$+$W_Y$).

wherein $HLB_X$ and $HLB_Y$ represent the HLBs of the surfactant X and the surfactant Y, respectively, and $W_X$ and $W_Y$ represent the mass fractions of the surfactant X and the surfactant Y, respectively.

When three or more nonionic surfactants are used in combination, the HLB of the mixture of the nonionic surfactants can be calculated by applying the above mutatis mutandis. In the present invention, it is preferable that the HLB of a nonionic surfactant prepared by mixing be within the above range. A nonionic surfactant whose HLB is out of a range of from 10 to 20 may also be used.

Examples of the nonionic surfactants as the component (F) include a glycerol fatty acid ester, a sorbitan fatty acid ester, a propylene glycol fatty acid ester, a polyethylene glycol fatty acid ester, a sucrose fatty acid ester, a polyoxyethylene fatty acid ester, a polyoxyethylene sorbitan fatty acid ester, a polyoxyethylene alkyl ether, a polyoxyethylene sorbitol a fatty acid ester, a polyoxyethylene glycerol fatty acid ester, a polyoxyethylene propylene glycol fatty acid ester, a polyoxyethylene castor oil, a polyoxyethylene hydrogenated castor oil, a polyoxyethylene hydrogenated castor oil fatty acid ester, a polyoxyethylene phytostanol ether, a polyoxyethylene phytosterol ether, a polyoxyethylene cholestanol ether, a polyoxyethylene cholesteryl ether, a polyoxyalkylene-modified organopolysiloxane and a polyoxyalkylene/alkyl co-modified organopolysiloxane.

Of them, in consideration of stability, a polyoxyethylene hydrogenated castor oil in which the average number of moles of the oxyethylene group added is from 25 to 80, a polyoxyethylene fatty acid ester in which the average number of moles of the oxyethylene group added is from 10 to 140, a polyoxyethylene sorbitan fatty acid ester with an alkyl group having 12 to 18 carbon atoms in which the average number of moles of the oxyethylene group added is 20, a polyoxyethylene alkyl ether with an alkyl group having 16 to 22 carbon atoms in which the average number of moles of the oxyethylene group added is from 15 to 25, and a polyoxyethylene/methyl polysiloxane copolymer in which the average number of moles of the oxyethylene group added is from 10 to 20 are preferred. Polyoxyethylene hydrogenated castor oil in which the average number of moles of the oxyethylene group added is from 25 to 80 and polyoxyethylene alkyl ether with an alkyl group having 16 to 22 carbon atoms in which the average number of moles of the oxyethylene group added is from 15 to 25 are more preferred. Polyoxyethylene hydrogenated castor oil in which the average number of moles of the oxyethylene group added is from 35 to 65 and polyoxyethylene alkyl ether with an alkyl group having 16 to 20 carbon atoms in which the average number of moles of the oxyethylene group added is from 20 to 25 are further preferred.

As the component (F), commercially available products, e.g., EMANONE CH-40 (HLB 12.5, manufactured by KAO CORPORATION) may be used as polyoxyethylene hydrogenated castor oil (40EO), EMANONE CH-60 (K) (HLB 14.0, manufactured by KAO CORPORATION) may be used as polyoxyethylene hydrogenated castor oil (60EO), EMALEX 1620 (HLB 14, manufactured by Nihon-Emulsion Co., Ltd.) may be used as polyoxyethylene isocetyl ether (20EO), and EMALEX 1825 (HLB 14, manufactured by Nihon-Emulsion Co., Ltd.) may be used as polyoxyethylene isostearyl ether (25EO).

One or more of these may be used as the component (F).

The content of the component (F) in the dispersion of fine lipid particles of the present invention is preferably 0.01% by mass or more, more preferably 0.05% by mass or more, and further preferably 0.1% by mass or more, and preferably 10% by mass or less, more preferably 5.0% by mass or less, and further preferably 1.0% by mass or less, in consideration of stability. The content is in a specific range of preferably 0.01% by mass or more and 10% by mass or less, more preferably 0.05% by mass or more and 5.0% by mass or less, and further preferably 0.1% by mass or more and 1.0% by mass or less.

The dispersion of fine lipid particles of the present invention is in the state of a dispersion in which the above component (A) and component (B) are dispersed and emulsified in water, and the dispersion of fine lipid particles has a pH of 3.5 or more and 8.0 or less. In the dispersion of fine lipid particles of the present invention, the particles have low crystallinity and are stable at a pH of 3.5 or more and 8.0 or less including acidic conditions, and thus the dispersion provides an excellent feeling on use while maintaining homeostasis on the surface of the skin. The pH is more preferably 3.5 or more and 7.0 or less, further preferably 3.5 or more and 6.0 or less, and even more preferably 3.5 or more and 5.5 or less in consideration of homeostasis on the surface of the skin and feeling on use.

The dispersion of fine lipid particles of the present invention may further contain a base and/or an acid in order to adjust the pH to the above range.

The base is not particularly limited, and may be an organic base or an inorganic base.

One or more organic bases selected from the group consisting of a basic amino acid and an alkanol amine are preferred. More specifically, one or more organic bases selected from the group consisting of basic amino acids such as L-arginine, lysine and histidine; and alkanol amines such as monoethanolamine, diethanolamine, triethanolamine, aminomethyl propanol, aminomethyl propanediol, aminoethyl propanediol and trishydroxymethylaminoethane are preferred.

One or more inorganic bases selected from the group consisting of calcium hydroxide, sodium hydroxide and potassium hydroxide are preferred.

Of them, one or more selected from the group consisting of L-arginine, calcium hydroxide, sodium hydroxide and potassium hydroxide are more preferred.

Furthermore, the acid may be an organic acid or an inorganic acid.

One or more organic acids selected from the group consisting of monocarboxylic acid, dicarboxylic acid, oxycarboxylic acid and acidic amino acid are preferred. More specifically, one or more organic acids selected from the group consisting of monocarboxylic acids such as acetic acid, propionic acid and butyric acid; dicarboxylic acids such as succinic acid, phthalic acid, fumaric acid, oxalic acid, malonic acid, glutaric acid and adipic acid; oxycarboxylic acids such as glycolic acid, citric acid, lactic acid, pyruvic acid, malic acid and tartaric acid; and acidic amino acids such as glutamic acid and aspartic acid are preferred.

One or more inorganic acids selected from the group consisting of hydrochloric acid, nitric acid, nitrous acid, sulfuric acid, sulfurous acid, phosphoric acid, phosphoric acid and phosphinic acid are preferred.

Of them, one or more selected from the group consisting of adipic acid and phosphorous acid are more preferred.

It is preferable that these bases and/or acids be included in the dispersion of fine lipid particles of the present invention in an amount such that the pH of the dispersion is in the above range.

The dispersion of fine lipid particles of the present invention may also contain, in addition to the above components, components used for conventional cosmetics, such as an oil component, a moisturizing agent, an antioxidant, an antiseptic, a chelating agent, a whitening agent, an ultraviolet absorber, vitamins, plant extract, various pharmaceutical active ingredients, a powder, a perfume and a color material.

The dispersion of fine lipid particles of the present invention may be prepared, for example, by mixing oil components including the components (A) to (D), dissolving them by heating at from 80 to 95° C., adding (E) water thereto, and stirring and emulsifying the mixture until homogeneous. Alternatively, the dispersion of fine lipid particles of the present invention may be prepared by an emulsifying method using a micromixer (as disclosed in JP-B-5086583). In this method, oil components and aqueous components classified from the components (A) to (E) and other components used as necessary are separately dissolved by heating; the resulting oil phase mixture and aqueous phase mixture are allowed to flow at respective constant rates and integrated with each other; and the resulting mixture is passed through pores having a pore diameter of 0.03 mm or more and 20 mm or less.

The dispersion of fine lipid particles of the present invention is a composition in which fine lipid particles including the component (A) and the component (B) are homogeneously emulsified and dispersed in water with low crystallinity. Whether or not the fine lipid particles are in the state of fine particles with low crystallinity may be observed by a dynamic light scattering method and differential scanning calorimetry. That is, first the presence of fine lipid particles and their particle size can be determined by the cumulant diameter measured by the dynamic light scattering method. Furthermore, the low crystallinity of fine lipid particles can be confirmed by the fact that the heat of fusion in a temperature range of 45° C. or more and 80° C. or less in differential scanning calorimetry is 0.30 J/g or less.

The average particle size of fine lipid particles emulsified and dispersed in the dispersion of fine lipid particles of the present invention is less than 200 nm, and in consideration of stability, more preferably less than 150 nm, and further preferably less than 130 nm.

Since fine lipid particles are homogeneously emulsified and dispersed in water with low crystallinity in the dispersion of fine lipid particles of the present invention, the dispersion not only improves feeling on use such as moist feeling but also makes the touch of the skin after application soft, fresh and smooth without stickiness, compared with conventional formulations which do not contain fine lipid particles. Thus, the dispersion is useful as a skin cosmetic. Furthermore, since fine lipid particles are homogeneously emulsified and dispersed in water with low crystallinity, it can be considered that the fine lipid particles have high membrane fluidity, and thus high permeability of active ingredients into the stratum corneum and a high effect of improving barrier function can be expected.

For the embodiments described above, the present invention also discloses the following compositions.

<1> A dispersion of fine lipid particles, comprising the following components (A) to (E), wherein the dispersion has a pH of 3.5 or more and 8.0 or less and the fine lipid particles have a heat of fusion of 0.30 J/g or less in a temperature range of 45° C. or more and 80° C. or less and an average particle size of less than 200 nm:

(A) one or more selected from the group consisting of a sterol and a derivative thereof, (B) a lipid other than the component (A), the lipid being solid or semi-solid at 25° C., (C) an anionic surfactant, (D) a water-soluble solvent, and (E) water <2> The dispersion of fine lipid particles according to <1>, wherein the component (A) comprises one or more selected from the group consisting of cholesterol, phytosterol and a derivative thereof, and more preferably the component (A) comprises one or more selected from the group consisting of cholesterol, fatty acid cholesterol ester, fatty acid phytosterol ester, cholesterol ester of N-acylamino acid and phytosterol ester of N-acylamino acid.

<3> The dispersion of fine lipid particles according to <1> or <2>, wherein the content of the component (A) is preferably 0.003% by mass or more, more preferably 0.08% by mass or more, further preferably 0.2% by mass or more, even more preferably 0.3% by mass or more, and still more preferably 0.4% by mass or more, and preferably 5.0° by mass or less, more preferably 1.0° by mass or less, further preferably 0.8% by mass or less, and even more preferably 0.6% by mass or less, and preferably 0.003% by mass or more and 5.0% by mass or less, more preferably 0.08% by mass or more and 1.0% by mass or less, further preferably 0.2% by mass or more and 0.8% by mass or less, even more preferably 0.3% by mass or more and 0.8% by mass or less, and still more preferably 0.4% by mass or more and 0.6% by mass or less.

<4> The dispersion of fine lipid particles according to any of <1> to <3>, wherein the component (B) comprises one or more selected from the group consisting of ceramides, sphingosines, a fatty acid having 16 to 22 carbon atoms and an aliphatic alcohol having 12 to 30 carbon atoms.

<5> The dispersion of fine lipid particles according to <4>, wherein the ceramides comprise a compound selected from the following formulas (1) and (2):

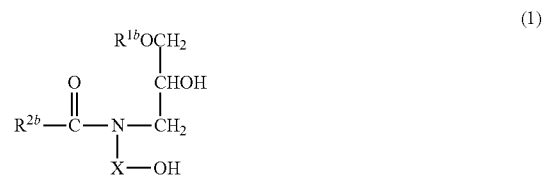

wherein Rib represents a hydrocarbon group having 10 to 26 carbon atoms, $R^{2b}$ represents a hydrocarbon group having 9 to 25 carbon atoms, and X represents —$(CH_2)_n$— (wherein n is an integer of from 2 to 6).

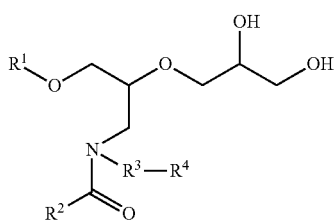

(2)

wherein $R^1$ and $R^2$ are the same or different and represent an optionally hydroxylated hydrocarbon group having 1 to 40 carbon atoms, $R^3$ represents an alkylene group having 1 to 6 carbon atoms or a single bond, $R^4$ represents a hydrogen atom, an alkoxy group having 1 to 12 carbon atoms or a 2,3-dihydroxypropyloxy group, with a proviso that, when $R^3$ is a single bond, $R^4$ is a hydrogen atom.

<6> The dispersion of fine lipid particles according to any of <1> to <5>, wherein the content of the component (B) is preferably 0.01% by mass or more, more preferably 0.1% by mass or more, and further preferably 0.3% by mass or more, and preferably 5.0% by mass or less, more preferably 3.0% by mass or less, and further preferably 1.0% by mass or less, and preferably 0.01% by mass or more and 5.0% by mass or less, more preferably 0.1% by mass or more and 3.0% by mass or less, and further preferably 0.3% by mass or more and 1.0% by mass or less.

<7> The dispersion of fine lipid particles according to any of <1> to <6>, wherein the mass ratio of the component (A) to the component (B), (A/B), is preferably 0.1 or more, more preferably 0.2 or more, and further preferably 0.3 or more, and preferably 1.0 or less, more preferably 0.8 or less, and further preferably 0.6 or less, and preferably 0.1 or more and 1.0 or less, more preferably 0.2 or more and 0.8 or less, and further preferably 0.3 or more and 0.6 or less.

<8> The dispersion of fine lipid particles according to any of <1> to <7>, wherein the component (C) comprises preferably one or more selected from the group consisting of an N-acylamino acid salt, an N-acylmethyltaurine salt, an alkyl phosphate, a polyoxyethylene alkyl ether phosphate, a fatty acid salt, an alkyl sulfate ester salt, a polyoxyethylene alkyl ether sulfate, an alkyl ether carboxylate, a dialkyl sulfosuccinate and a diacylamino acid lysine salt, more preferably one or more selected from the group consisting of an N-acylamino acid salt, an N-acylmethyltaurine salt, a polyoxyethylene alkyl ether phosphate, a fatty acid salt, a diacylamino acid lysine salt, an alkyl sulfate ester salt, a polyoxyethylene alkyl ether sulfate, an alkyl ether carboxylate and a dialkyl sulfosuccinate, further preferably one or more selected from the group consisting of an N-acylamino acid salt, an N-acylmethyltaurine salt, a polyoxyethylene alkyl ether phosphate, a fatty acid salt, a diacylamino acid lysine salt, a polyoxyethylene alkyl ether sulfate, an alkyl ether carboxylate and a dialkyl sulfosuccinate, still more preferably one or more selected from the group consisting of an N-acylamino acid salt, an N-acylmethyltaurine salt, a polyoxyethylene alkyl ether phosphate, a fatty acid salt and a diacylamino acid lysine, and particularly preferably one or more selected from an N-acylamino acid salt and an N-acylmethyltaurine salt.

<9> The dispersion of fine lipid particles according to any of <1> to <8>, wherein the content of the component (C) is preferably 0.002% by mass or more, more preferably 0.05% by mass or more, further preferably 0.1% by mass or more, and preferably 3.0% by mass or less, more preferably 1.0% by mass or less, further preferably 0.5° by mass or less, and preferably 0.02% by mass or more and 3.0% by mass or less, more preferably 0.05% by mass or more and 1.0% by mass or less, and further preferably 0.1% by mass or more and 0.5% by mass or less.

<10> The dispersion of fine lipid particles according to any of <1> to <9>, wherein the total mass of the component (A), the component (B) and the component (C) is preferably 0.015% by mass or more, more preferably 0.33% by mass or more, and further preferably 0.5% by mass or more, and preferably 13.0% by mass or less, more preferably 5.0% by mass or less, further preferably 2.0% by mass or less, and preferably 0.015% by mass or more and 13.0% by mass or less, more preferably 0.33% by mass or more and 5.0% by mass or less, and further preferably 0.5% by mass or more and 2.0% by mass or less.

<11> The dispersion of fine lipid particles according to any of <1> to <10>, wherein the ratio of the total mass of the component (A) and the component (B) to the mass of the component (C), ((A+B)/C), is preferably 0.05 or more, more preferably 0.5 or more, further preferably 1.0 or more, even more preferably 2.0 or more, and preferably 6.0 or less, more preferably 5.5 or less, and further preferably 5.0 or less, and preferably 0.05 or more and 6.0 or less, more preferably 0.5 or more and 5.5 or less, further preferably 1.0 or more and 5.5 or less, and even more preferably 2.0 or more and 5.5 or less.

<12> The dispersion of fine lipid particles according to any of <1> to <11>, wherein the component (D) comprises one or more selected from a polyhydric alcohol and a lower alcohol, and preferably one or more selected from the group consisting of ethanol, glycerol, 1,3-butylene glycol, dipropylene glycol and 1,3-propanediol.

<13> The dispersion of fine lipid particles according to any of <1> to <12>, wherein the content of the component (D) is preferably 1.0% by mass or more, more preferably 2.0% by mass or more, and further preferably 3.0% by mass or more, and preferably 30% by mass or less, more preferably 25% by mass or less, and further preferably 20% by mass or less, and preferably 1.0% by mass or more and 30% by mass or less, more preferably 2.0% by mass or more and 25% by mass or less, and further preferably 3.0% by mass or more and 20% by mass or less.

<14> The dispersion of fine lipid particles according to any of <7> to <13>, wherein the content of the component (E) is preferably 50% by mass or more, more preferably 70% by mass or more, and further preferably 80% by mass or more, and preferably 97% by mass or less, more preferably 95% by mass or less, and further preferably 90% by mass or less, and preferably 50% by mass or more and 97% by mass or less, more preferably 70% by mass or more and 95% by mass or less, and further preferably 80% by mass or more and 90% by mass or less.

<15> The dispersion of fine lipid particles according to any of <1> to <14>, further comprising a component (F), a nonionic surfactant.

<16> The dispersion of fine lipid particles according to <15>, wherein the component (F) comprises preferably a nonionic surfactant having an HLB of from 10 to 20, more preferably a nonionic surfactant having an HLB of from 12 to 15, and further preferably a nonionic surfactant having an HLB of from 12.5 to 14.5.

<17> The dispersion of fine lipid particles according to <15> or <16>, wherein the component (F) comprises one or more selected from the group consisting of a glycerol fatty acid ester, a sorbitan fatty acid ester, a propylene glycol fatty acid ester, a polyethylene glycol fatty acid ester, a sucrose fatty acid ester, a polyoxyethylene fatty acid ester, a polyoxyethylene sorbitan fatty acid ester, a polyoxyethylene alkyl ether, a polyoxyethylene sorbitol fatty acid ester, a polyoxyethylene glycerol fatty acid ester, a polyoxyethylene propylene glycol fatty acid ester, a polyoxyethylene castor oil, a polyoxyethylene hydrogenated castor oil, a polyoxyethylene hydrogenated castor oil fatty acid ester, a polyoxyethylene phytostanol ether, a polyoxyethylene phytosterol ether, a polyoxyethylene cholestanol ether, a polyoxyethylene cholesteryl ether, a polyoxyalkylene-modified organopolysiloxane and a polyoxyalkylene/alkyl co-modified organopolysiloxane.

<18> The dispersion of fine lipid particles according to any of <15> to <17>, wherein the content of the component (F) is preferably 0.01° by mass or more, more preferably 0.05% by mass or more, and further preferably 0.1% by mass or more, and preferably 10% by mass or less, more preferably 5.0% by mass or less, further preferably 1.0% by mass or less, and preferably 0.01% by mass or more and 10% by mass or less, further preferably 0.05% by mass or more and 5.0% by mass or less, and further preferably 0.1% by mass or more and 1.0% by mass or less.

<19> The dispersion of fine lipid particles according to any of <1> to <18>, wherein the dispersion has a pH of preferably 3.5 or more and 7.0 or less, more preferably 3.5 or more and 6.0 or less, and further preferably 3.5 or more and 5.5 or less.

<20> The dispersion of fine lipid particles according to any of <1> to <19>, wherein the fine lipid particles comprising the component (A) and the component (B) are homogeneously emulsified and dispersed in water with low crystallinity.

<21> The dispersion of fine lipid particles according to any of <1> to <20>, wherein the fine lipid particles comprising the component (A) and the component (B) and being emulsified and dispersed in the dispersion of fine lipid particles, have an average particle size of preferably less than 150 nm, more preferably less than 130 nm.

<22> A skin cosmetic comprising the dispersion of fine lipid particles according to any of <1> to <21>.

Examples

Next, the present invention will be described in more detail with reference to Examples.

(Method of Production)

(1) Micromixer Method

For the compositions described in Tables 1 to 4, and 7 to 8 and the composition of Example 17 described in Table 6, first the components A, B, D and F were dissolved by heating at 85° C. to prepare a homogeneous oil phase mixture X. Next, the components C and E were dissolved by heating at 85° C. to prepare a homogeneous water phase mixture Y. The mixtures X and Y were respectively allowed to flow at a pressure of 0.2 MPa·s at respective constant rates while heating at 85° C., and the mixtures were integrated with each other and passed through pores having a pore size of 0.4 mm to give a homogeneous emulsified product Z in the form of toner. Part of the components D, E and components other than the components A to F were mixed, and after it was confirmed that the components were homogeneously dissolved, the mixture was added to the emulsified product Z to give a sample.

(2) Beaker Method

For the compositions described in Table 5 and the composition of Comparative Example 6 described in Table 6, the components A, B, C, D and F were dissolved by heating at 85° C. to prepare a homogeneous oil phase mixture. The component E was added dropwise to the oil phase mixture with stirring to give an emulsified product. Part of the component E and components other than the components A to F were mixed, and after confirming that the components were homogeneously dissolved, the mixture was added to the emulsified product to give a sample.

(Method of evaluation)

(1) State of Particles

The cumulant diameter of the dispersions of fine lipid particles of Examples and Comparative Examples was determined given by the measurement (a 20-fold dilute solution) by a dynamic light scattering method using a particle size analyzer (Zetasizer Nano ZS manufactured by Malvern Panalytical Ltd.). The results were ranked according to the following A to D.

A: Less than 130 nm
B: 130 nm or more and less than 150 nm
C: 150 nm or more and less than 200 nm
D: 200 nm or more (2) State of Crystal The heat of fusion of the dispersions of fine lipid particles of Examples and Comparative Examples was determined based on the total amount of heat absorbed in a temperature range of 45° C. or more and 80° C. or less in a melting curve obtained by the measurement (temperature increase rate: 0.3° C./minute) using a differential scanning calorimeter (μDSC VII evo manufactured by Rigaku Corporation). The results were ranked according to the following A to D.

A: Heat of fusion of less than 0.05 J/g
B: Heat of fusion of 0.05 J/g or more and less than 0.15 J/g
C: Heat of fusion of 0.15 J/g or more and 0.30 J/g or less
D: Heat of fusion of more than 0.30 J/g (3) Stability The dispersions of fine lipid particles of Examples and Comparative Examples were put in standard glass containers (Mighty Vial No. 7 manufactured by AS ONE Corporation) and stored in an environment of room temperature and in an environment of 50° C. for a month. The change in appearance was observed and evaluated. In the observation, no occurrence of phase separation, no occurrence of creaming, and the absence of sedimentation or precipitation in the formulation were checked. Only the formulations with no change was determined as "pass".

(4) Feeling on Use

Expert panelists assessed the feeling on use including "moist feeling", "softness" and "smoothness" by criteria with 4 ratings in descending order, when a prescribed amount of each dispersion of Example and Comparative Example described in Table 6 was applied to the skin. The criteria of evaluation are shown below.

A: Significantly felt
B: Moderately felt
C: Slightly felt
D: Not felt at all

The dispersions of fine lipid particles described in Tables 1 to 8 were prepared, and their properties, stability and feeling on use were assessed. The results are also shown in Tables 1 to 8.

TABLE 1

| | | Example | | | | Comparative Example |
|---|---|---|---|---|---|---|
| Component | | 1 | 2 | 3 | 4 | 1 |
| B | N-(hexadecyloxyhydroxypropyl)-N-hydroxyethylhexadecanamide *1 | 1 | 1 | 1 | 1 | 1 |

TABLE 1-continued

|   | Component | Example 1 | Example 2 | Example 3 | Example 4 | Comparative Example 1 |
|---|---|---|---|---|---|---|
| A | Cholesterol | 0.2 | 0.3 | 0.4 | 0.6 | — |
| C | Sodium N-stearoyl-N-methyltaurine *2 | 0.3 | 0.3 | 0.3 | 0.3 | 0.3 |
| F | Polyoxyethylene hydrogenated castor oil *3 | 0.2 | 0.2 | 0.2 | 0.2 | 0.2 |
| D | Dipropylene glycol | 5.0 | 5.0 | 5.0 | 5.0 | 5.0 |
| E | Purified water | 93.2 | 93.2 | 93.1 | 92.9 | 93.5 |
|   | Total | 100 | 100 | 100 | 100 | 100 |
|   | Method of production | Micromixer method | Micromixer method | Micromixer method | Micromixer method | Micromixer method |
|   | State of crystal | C | B | A | A | D |
|   | (accumulated amount of heat at 45° C. to 80° C.) | 0.26 J/g | 0.12 J/g | 0.4 J/g | 0.0005 J/g | 0.77 J/g |

*1 Sphingolipid E (manufactured by KAO CORPORATION)
*2 Nikkol SMT (manufactured by Nikko Chemicals Co., Ltd.)
*3 EMANONE CH-60K (manufactured by KAO CORPORATION)

TABLE 2

|   | Component | Example 5 | Example 6 | Comparative Example 2 | Comparative Example 3 |
|---|---|---|---|---|---|
| B | N-(hexadecyloxyhydroxypropyl)-N-hydroxyethylhexadecanamide *1 | 0.8 | 0.8 | 1.1 | 0.8 |
| A | Cholesterol | 0.3 | 0.3 | — | 0.3 |
| C | Sodium N-stearoyl-N-methyltaurine *2 | 0.3 | 0.3 | 0.3 | — |
| F | Polyoxyethylene hydrogenated castor oil *3 | 0.2 | — | 0.2 | 0.2 |
| D | Dipropylene glycol | 3.0 | 3.0 | 3.0 | 3.0 |
|   | 86% glycerol | 10.0 | 10.0 | 10.0 | 10.0 |
| E | Purified water | 85.4 | 85.6 | 85.4 | 85.7 |
|   | Total | 100 | 100 | 100 | 100 |
|   | Method of production | Micromixer method | Micromixer method | Micromixer method | Micromixer method |
|   | pH | 6.7 | 6.8 | 6.9 | 6.7 |
|   | State of particles | A | A | A | D |
|   | (particle size) | 92.6 nm | 90.6 nm | 68.9 nm | 486.6 nm |
|   | State of crystal | A | A | D | D |
|   | Stability | RT to 50° C. 1M "Pass" | RT to 50° C. 1M "Pass" | RT1M "Fail" | 50° C. 1M "Fail" |

*1 Sphingolipid E (manufactured by KAO CORPORATION)
*2 Nikkol SMT (manufactured by Nikko Chemicals Co., Ltd.)
*3 EMANONE CH-60K (manufactured by KAO CORPORATION)

TABLE 3

|   | Component | Example 7 | Example 8 | Comparative Example 4 | Comparative Example 5 |
|---|---|---|---|---|---|
| B | N-(hexadecyloxyhydroxypropyl)-N-hydroxyethylhexadecanamide *1 | 0.8 | 0.8 | 1.1 | 0.8 |
| A | Cholesterol | 0.3 | 0.3 | — | 0.3 |
| C | Sodium N-stearoyl-N-methyltaurine *2 | 0.3 | 0.3 | 0.3 | — |
| F | Polyoxyethylene hydrogenated castor oil *3 | 0.2 | — | 0.2 | 0.2 |
| D | Dipropylene glycol | 3.0 | 3.0 | 3.0 | 3.0 |
|   | 86% glycerol | 10.0 | 10.0 | 10.0 | 10.0 |
|   | Adipic acid | 0.05 | 0.05 | 0.05 | 0.05 |
| E | Purified water | 85.35 | 85.55 | 85.35 | 85.65 |
|   | Total | 100 | 100 | 100 | 100 |
|   | Method of production | Micromixer method | Micromixer method | Micromixer method | Micromixer method |
|   | pH | 3.6 | 3.7 | 3.7 | 3.7 |
|   | State of particles | A | A | A | D |
|   | (particle size) | 93.2 nm | 91.6 nm | 70.0 nm | 486.7 nm |
|   | State of crystal | A | A | D | D |

TABLE 3-continued

|  | | Example | | Comparative Example | |
|---|---|---|---|---|---|
| Component | | 7 | 8 | 4 | 5 |
| Stability | | RT to 50° C. 1M "Pass" | RT to 50° C. 1M "Pass" | RT1M "Fail" | 50° C. 1M "Fail" |

*1 Sphingolipid E (manufactured by KAO CORPORATION)
*2 Nikkol SMT (manufactured by Nikko Chemicals Co., Ltd.)
*3 EMANONE CH-60K (manufactured by KAO CORPORATION)

TABLE 4

|  | | | Example | | |
|---|---|---|---|---|---|
|  | Component | | 9 | 10 | 11 |
| B | N-(hexadecyloxyhydroxypropyl)-N-hydroxyethylhexadecanamide *1 | | 0.3 | 0.3 | 0.3 |
| A | Cholesterol | | 0.1 | 0.1 | 0.1 |
| C | Sodium N-stearoyl-N-methyltaurine *2 | | 0.1 | 0.1 | 0.1 |
| F | Polyoxyethylene hydrogenated castor oil *3 | | 0.1 | 0.1 | — |
| D | Dipropylene glycol | | 1.0 | 1.0 | 1.0 |
|  | Methylparaben | | 0.2 | — | 0.2 |
|  | Phenoxyethanol | | — | 0.4 | — |
| D | Glycerol | | 15.0 | 15.0 | 15.0 |
|  | L-arginine | | 0.05 | 0.05 | 0.05 |
|  | Adipic acid | | 0.05 | 0.05 | 0.05 |
|  | Allantoin | | 0.2 | 0.2 | 0.2 |
|  | Eucalyptus extract *4 | | 1.0 | 1.0 | 1.0 |
|  | Purified water | | 81.9 | 81.7 | 82.0 |
|  | Total | | 100 | 100 | 100 |
|  | Method of production | | Micromixer method | Micromixer method | Micromixer method |
|  | pH | | 4.4 | 4.6 | 4.6 |
|  | State of particles | | A | A | A |
|  | (particle size) | | 93.9 nm | 95.3 nm | 92.8 nm |
|  | State of crystal | | A | A | A |
|  | Stability | | RT to 50° C. 1M "Pass" | RT to 50° C. 1M "Pass" | RT to 50° C. 1M "Pass" |

*1 Sphingolipid E (manufactured by KAO CORPORATION)
*2 Nikkol SMT (manufactured by Nikko Chemicals Co., Ltd.)
*3 EMANONE CH-60K (manufactured by KAO CORPORATION)
*4 Eucalyptus extract K (manufactured by KOEI KOGYO CO., LTD.)

TABLE 5

|  | | | | Example | | | |
|---|---|---|---|---|---|---|---|
|  | Component | | 12 | 13 | 14 | 15 | 16 |
| B | N-(hexadecyloxyhydroxypropyl)-N-hydroxyethylhexadecanamide *1 | | 0.1 | 0.09 | 0.09 | 0.1 | 0.09 |
| A | Cholesterol | | 0.04 | 0.036 | 0.036 | 0.4 | 0.36 |
| C | Sodium N-lauroyl-N-methyltaurine *2 | | 1.0 | 0.9 | 0.9 | 1.0 | 0.9 |
|  | Dipropylene glycol | | 3.0 | 2.7 | — | — | 2.7 |
| D | Glycerol | | 10.0 | 9.0 | 9.0 | — | — |
|  | Ethanol | | — | — | — | 10.0 | 9.0 |
|  | L-arginine | | — | — | 0.05 | — | — |
|  | Adipic acid | | — | 0.05 | 0.05 | — | 0.05 |
| E | Purified water | | 85.86 | 87.224 | 89.874 | 88.5 | 86.9 |
|  | Total | | 100 | 100 | 100 | 100 | 100 |
|  | Method of production | | Beaker method | Beaker method | Beaker method | Beaker method | Beaker method |
|  | pH | | 6.9 | 3.8 | 4.8 | 7.0 | 3.9 |
|  | State of particles | | A | A | A | A | A |
|  | (particle size) | | 36.4 nm | 36.7 nm | 36.5 nm | 34.5 nm | 34.9 nm |
|  | State of crystal | | A | A | A | A | A |
|  | Stability | | RT to 50° C. 1M "Pass" | RT to 50° C. 1M "Pass" | RT to 50° C. 1M "Pass" | RT to 50° C. 1M "Pass" | RT to 50° C. 1M "Pass" |

*1 Sphingolipid E (manufactured by KAO CORPORATION)
*2 Nikkol SMT (manufactured by Nikko Chemicals Co., Ltd.)

TABLE 6

| Component | | Example 17 | Comparative Example 6 |
|---|---|---|---|
| B | N-(hexadecyloxyhydroxypropyl)-N-hydroxyethylhexadecanamide *1 | 0.75 | — |
| A | Cholesterol | 0.3 | — |
| C | Sodium N-stearoyl-N-methyltaurine *2 | 0.26 | 0.26 |
| F | Polyoxyethylene hydrogenated castor oil *3 | 0.17 | 0.17 |
| D | Dipropylene glycol | 2.61 | 2.61 |
| | 86% glycerol | 10.0 | 10.0 |
| | Adipic acid | 0.05 | 0.05 |
| E | Purified water | 85.86 | 86.91 |
| | Total | 100 | 100 |
| | Method of production | Micromixer method | Micromixer method |
| | Feeling on use — Moist feeling | A | C |
| | Softness | A | D |
| | Smoothness | B | D |

*1 Sphingolipid E (manufactured by KAO CORPORATION)
*2 Nikkol SMT (manufactured by Nikko Chemicals Co., Ltd.)
*3 EMANONE CH-60K (manufactured by KAO CORPORATION)

Also in the dispersions of fine lipid particles described in Table 7, fine particles of solid lipid such as ceramides are emulsified and dispersed in a stable manner with low crystallinity, and the dispersions have excellent stability and feeling on use.

TABLE 7

| Component | | Example 18 | Example 19 |
|---|---|---|---|
| B | N-(hexadecyloxyhydroxypropyl)-N-hydroxyethylhexadecanamide *1 | — | 0.01 |
| | Ceramide 2 | 0.01 | — |
| A | Cholesterol | 0.1 | — |
| | Phytosterol | — | 0.1 |
| C | Sodium N-stearoyl-N-methyltaurine *2 | 0.1 | 0.1 |
| F | Polyoxyethylene hydrogenated castor oil *3 | 0.1 | 0.1 |
| D | Dipropylene glycol | 1.0 | 1.0 |
| | Methylparaben | 0.2 | 0.2 |
| D | Glycerol | 15.0 | 15.0 |
| | L-arginine | 0.05 | 0.05 |
| | Adipic acid | 0.05 | 0.05 |
| | Allantoin | 0.2 | 0.2 |
| | Eucalyptus extract *4 | 1.0 | 1.0 |
| | Purified water | 82.28 | 82.28 |
| | Total | 100 | 100 |
| | Method of production | Micromixer method | Micromixer method |

*1 Sphingolipid E (manufactured by KAO CORPORATION)
*2 Nikkol SMT (manufactured by Nikko Chemicals Co., Ltd.)
*3 EMANONE CH-60K (manufactured by KAO CORPORATION)
*4 Eucalyptus extract K (manufactured by KOEI KOGYO CO., LTD.)

TABLE 8

| Component | | Example 1 | Example 20 |
|---|---|---|---|
| B | N-(hexadecyloxyhydroxypropyl)-N-hydroxyethylhexadecanamide *1 | 1 | 1 |
| A | Cholesterol | 0.2 | 0.4 |
| C | Sodium N-stearoyl-N-methyltaurine *2 | 0.3 | — |
| | Stearoyl glutamic acid *6 | — | 0.3 |
| F | Polyoxyethylene hydrogenated castor oil *3 | 0.2 | 0.2 |
| D | Dipropylene glycol | 5.0 | 5.0 |
| E | Purified water | 93.3 | 92.9 |
| | Total | 100 | 100 |
| | Method of production | Micromixer method | Micromixer method |
| | State of crystal | C | B |
| | (accumulated amount of heat at 45° C. to 80° C. | 0.26 J/g | 0.06 J/g |

*1 Sphingolipid E (manufactured by KAO CORPORATION)
*2 Nikkol SMT (manufactured by Nikko Chemicals Co., Ltd.)
*3 EMANONE CH-60K (manufactured by KAO CORPORATION)
*6 Amisoft HA-P (manufactured by Ajinomoto Co., Inc.)

The invention claimed is:

1. A dispersion of fine lipid particles, comprising:
   (A) at least one selected from the group consisting of a cholesterol and a phytosterol, in an amount of from 0.08% by mass to 0.6% by mass;
   (B) N-(hexadecyloxyhydroxypropyl)-N-hydroxyethyl-hexadecanamide, in an amount of from 0.01% by mass to 1% by mass;
   (C) at least one selected form the group consisting of sodium N-lauroyl-N-methyltaurate and sodium N-stearoyl-N-methyltaurate, in an amount of from 0.002% by mass to 1% by mass;
   (D) at least one selected form the group consisting of dipropylene glycol, glycerol, ethanol and 1,3-butylene glycol in an amount of from 3% by mass to 30% by mass; and
   (E) water,
   wherein a ratio of a total mass of the component (A) and the component (B) to a mass of the component (C), ((A+B)/C), is from 0.05 to 6.0,
   the dispersion has a pH of from 3.5 to 8.0, and
   the fine lipid particles have a heat of fusion of 0.30 J/g or less at a temperature of from 45° C. to 80° C. and an average particle size of less than 200 nm.

2. The dispersion of fine lipid particles according to claim 1, further comprising:
   (F) a nonionic surfactant.

3. A skin cosmetic, comprising:
the dispersion of fine lipid particles according to claim 1.

4. The dispersion of fine lipid particles according to claim 1, wherein the amount of the component (C) is from 0.05% by mass to 1.0% by mass.

5. The dispersion of fine lipid particles according to claim 1, wherein a total mass of the component (A), the component (B), and the component (C) is at least 0.33% by mass.

6. The dispersion of claim 1, wherein
the component (A) is the cholesterol and the amount of the component (A) is from 0.1% by mass to 0.6% by mass;
the component (B) is N-(hexadecyloxyhydroxypropyl)-N-hydroxyethylhexadecanamide and the amount of the component (B) is from 0.09% by mass to 1% by mass;
the components (C) is sodium N-stearoyl-N-methyltaurate and the amount of the component (C) is from 0.1% by mass to 1% by mass; and
the component (D) is at least one selected from the group consisting of dipropylene glycol, glycerol and ethanol and the amount of the component (D) is from 5% by mass to 16% by mass.

7. The dispersion of fine lipid particles according to claim 1, wherein the amount of the component (D) is from 3% by mass to 20% by mass.

* * * * *